United States Patent
Suehling et al.

(10) Patent No.: US 12,354,260 B2
(45) Date of Patent: Jul. 8, 2025

(54) METHOD FOR PROVIDING MEDICAL IMAGING DECISION SUPPORT DATA AND METHOD FOR PROVIDING GROUND TRUTH IN 2D IMAGE SPACE

(71) Applicant: Siemens Healthineers AG, Forchheim (DE)

(72) Inventors: Michael Suehling, Erlangen (DE); Felix Durlak, Hemhofen (DE); Rainer Kaergel, Stegaurach (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 294 days.

(21) Appl. No.: 17/899,798

(22) Filed: Aug. 31, 2022

(65) Prior Publication Data
US 2023/0070656 A1 Mar. 9, 2023

(30) Foreign Application Priority Data
Sep. 3, 2021 (EP) .................................... 21194700

(51) Int. Cl.
*G06T 7/00* (2017.01)
*G16H 30/40* (2018.01)

(52) U.S. Cl.
CPC ........... *G06T 7/0012* (2013.01); *G16H 30/40* (2018.01); *G06T 2207/30012* (2013.01)

(58) Field of Classification Search
CPC ........ G06T 7/0012; G06T 2207/30012; G16H 30/40; G16H 50/70; G16H 50/20
USPC .......................................................... 382/128
See application file for complete search history.

(56) References Cited

U.S. PATENT DOCUMENTS

| | | | |
|---|---|---|---|
| 8,917,923 B2 * | 12/2014 | Grosskopf | A61B 6/5294 382/131 |
| 10,957,442 B2 * | 3/2021 | Kalafut | G16H 30/40 |
| 2009/0161937 A1 * | 6/2009 | Peng | G06T 7/73 382/131 |
| 2018/0240551 A1 * | 8/2018 | Perrey | G16H 30/40 |
| 2019/0021677 A1 * | 1/2019 | Grbic | G06T 7/11 |
| 2020/0178920 A1 | 6/2020 | Grasruck et al. | |
| 2020/0320326 A1 | 10/2020 | Dou et al. | |
| 2020/0380680 A1 | 12/2020 | Aoyagi et al. | |
| 2021/0004960 A1 * | 1/2021 | Groth | A61B 5/743 |
| 2022/0037018 A1 * | 2/2022 | Goede | G06F 18/251 |

OTHER PUBLICATIONS

Amended claims filed after receipt of (European) search report dated Sep. 8, 2023 for EP21194700 (Year: 2023).*
Amendments received before examination dated Sep. 8, 2023 for EP21194700 (Year: 2023).*

(Continued)

Primary Examiner — Juan A Torres
(74) Attorney, Agent, or Firm — Harness, Dickey & Pierce, P.L.C.

(57) ABSTRACT

One or more example embodiments of the present invention relates in one aspect to a computer-implemented method includes receiving 2D topogram data of a patient; generating 2D topogram annotation data by applying a machine learning algorithm for topogram analysis onto the 2D topogram data; generating the medical imaging decision support data based on the 2D topogram annotation data; and providing the medical imaging decision support data.

11 Claims, 3 Drawing Sheets

(56) References Cited

OTHER PUBLICATIONS

European search opinion dated May 10, 2022 for EP 21194700. (Year: 2022).*
European search report dated May 10, 2022 for EP 21194700 (Year: 2022).*
Provisional opinion accompanying the partial search results dated Feb. 25, 2022 for EP21194700. (Year: 2022).*
Partial European search report date Feb. 25, 2022 for EP 21194700. (Year: 2022).*
Zhang, Yue et al.: "Task Driven Generative Modeling for Unsupervised Domain Adaptation: Application to X-ray Image Segmentation"; arXiv:1806.07201v1; 2018.

* cited by examiner

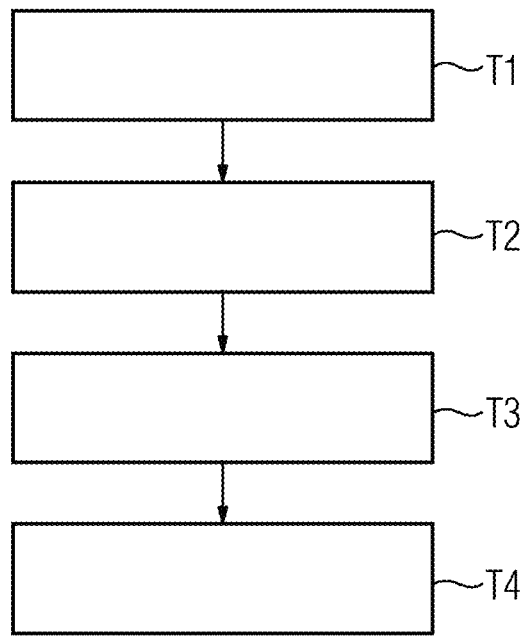
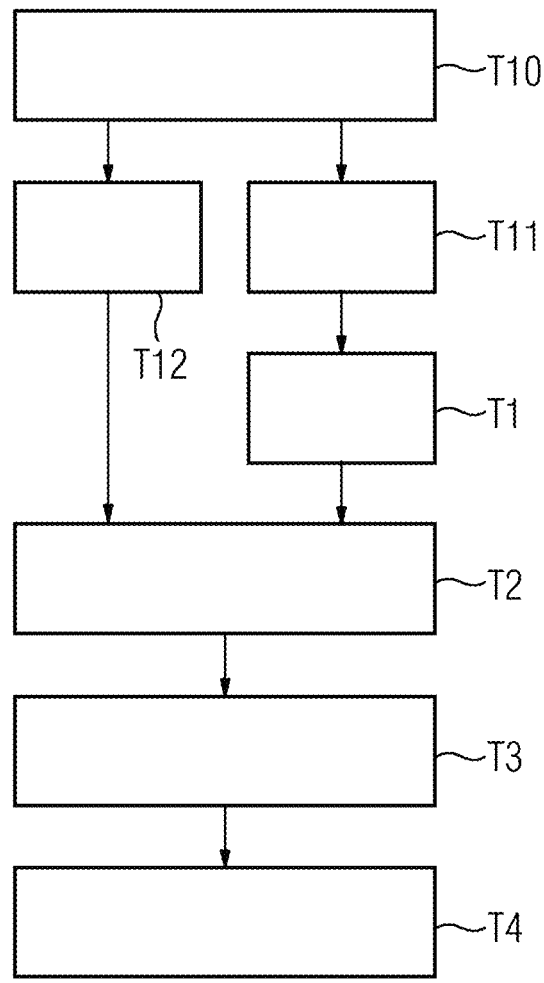
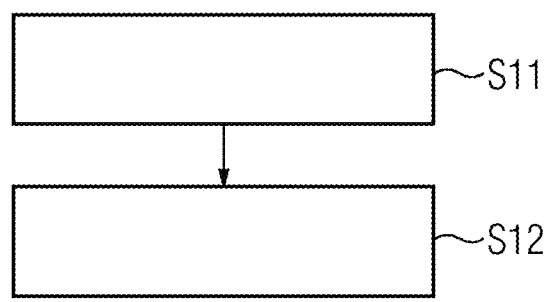

METHOD FOR PROVIDING MEDICAL IMAGING DECISION SUPPORT DATA AND METHOD FOR PROVIDING GROUND TRUTH IN 2D IMAGE SPACE

CROSS-REFERENCE TO RELATED APPLICATION(S)

The present application claims priority under 35 U.S.C. § 119 to European Patent Application No. 21194700.7, filed Sep. 3, 2021, the entire contents of which are incorporated herein by reference.

FIELD

One or more example embodiments of the present invention relates to a computer-implemented method for providing medical imaging decision support data. Further example embodiments relate to a computer-implemented method for providing a training pair for a training of a machine learning algorithm, to a computer-implemented method for training a machine learning algorithm for topogram analysis, to a data processing system, a medical imaging device, a computer program product and a computer-readable storage medium.

BACKGROUND

In computed tomography (CT), 2D topograms (also called scanograms or scouts) are acquired prior to 3D image acquisition. Currently, the main purpose of the topogram projection images is to plan the scan range and reconstruction field of view (FoV) for the 3D CT scan to be performed and to estimate the CT dose modulation for automatic exposure control. However, human diagnostic image reading is predominantly based on 3D images. In daily clinical routine, topogram images are only read sporadically with some findings being missed by reading the 3D images only.

In particular, the reconstruction field of view of the 3D reconstructed images is typically smaller than the topogram scan range of the patient. For instance, in abdominal CT imaging, findings such as lung nodules or cardiomegaly may only be captured in the topogram images but are not included in the reduced 3D abdominal CT reconstruction field of view. In trauma imaging, findings such as skull fractures may be overlooked in 3D axial images while being obviously visible in the 2D projection topogram data.

Zhang Y., Miao S., Mansi T., Liao R. (2018) Task Driven Generative Modeling for Unsupervised Domain Adaptation: Application to X-ray Image Segmentation. In: Frangi A., Schnabel J., Davatzikos C., Alberola-Lopez C., Fichtinger G. (eds) Medical Image Computing and Computer Assisted Intervention—MICCAI 2018. MICCAI 2018. Lecture Notes in Computer Science, vol 11071. Springer, Cham, disclose an application of a task driven generative modeling approach to X-ray image segmentation.

SUMMARY

One or more example embodiments of the present invention improve the topogram-based analysis within a medical imaging examination. The problem is solved according to the independent claim. Further advantageous embodiments and additional advantageous features are described in the dependent claims and in the specification.

According to one or more example embodiments, a computer-implemented method includes receiving 2D topogram data of a patient; generating 2D topogram annotation data by applying a machine learning algorithm for topogram analysis onto the 2D topogram data; generating the medical imaging decision support data based on the 2D topogram annotation data; and providing the medical imaging decision support data.

According to one or more example embodiments, a computer-implemented method for providing a training pair for a training of a machine learning algorithm, the method comprising receiving 3D annotation data in relation to 3D image data of an examination region, the examination region comprising an anatomical structure, the 3D annotation data being indicative of a characteristic of the anatomical structure; receiving 2D projection image data, the 2D projection image data being related to the 3D image data through a projection geometry; generating 2D annotation data in relation to the 2D projection image data based on the projection geometry and the 3D annotation data, the 2D annotation data being indicative of the characteristic of the anatomical structure; and providing the training pair, the training pair comprising the 2D projection image data and the 2D annotation data.

According to one or more example embodiments, a computer-implemented method for training a machine learning algorithm for topogram analysis includes receiving a plurality of training pairs, each training pair of the plurality of training pairs being provided using a method according to one or more example embodiments; and training the machine learning algorithm based on the plurality of training pairs.

According to one or more example embodiments, a data processing system includes a data interface; and a processor, the data processing system being configured to perform a method according to one or more example embodiments.

According to one or more example embodiments, a medical imaging device comprises the data processing system.

According to one or more example embodiments, a non-transitory computer-readable storage medium, comprises instructions which, when the instructions are executed by a computer, cause the computer to perform a method according to one or more example embodiments.

BRIEF DESCRIPTION OF THE DRAWINGS

One or more example embodiments of the present invention will be illustrated below with reference to the accompanying figures using example embodiments. The illustration in the figures is schematic and highly simplified and not necessarily to scale.

FIG. 3 shows a flow chart for a method for providing a training pair according to an example embodiment.

FIG. 4 shows a flow chart for another example of a method for providing a training pair according to an example embodiment.

FIG. 5 shows a flow chart for a computer-implemented method for training a machine learning algorithm for topogram analysis according to an example embodiment.

DETAILED DESCRIPTION

Figure 1:
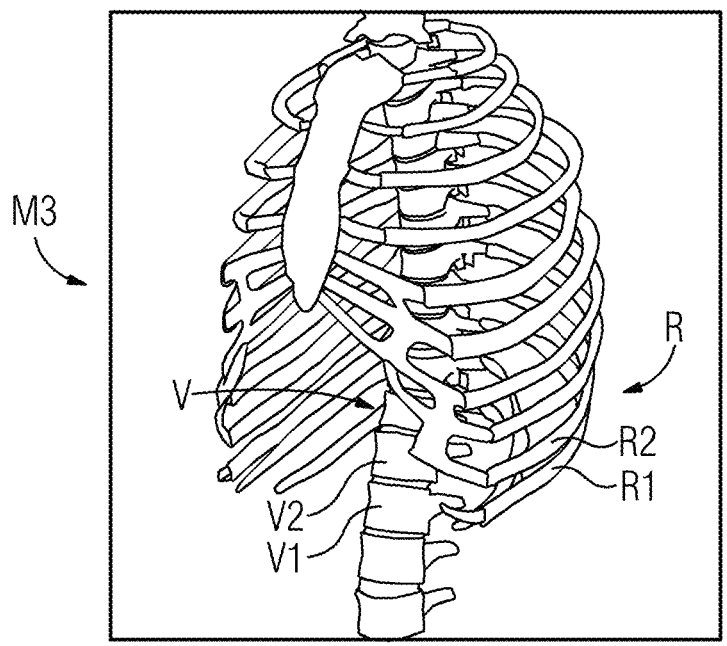
FIG. 1 shows an annotated 3D image according to an example embodiment.

One or more example embodiments of the present invention relates in one aspect to a computer-implemented method for providing medical imaging decision support data, the method comprising:

Receiving 2D topogram data of a patient,
Generating 2D topogram annotation data by applying a machine learning algorithm for topogram analysis onto the 2D topogram data,
Generating the medical imaging decision support data based on the 2D topogram annotation data, and
Providing the medical imaging decision support data.

The automated AI-based topogram analysis may be implemented, for example, in form of companion diagnostics for 3D image reading. In another aspect, the automatic AI-based topogram analysis is immediately performed after topogram acquisition. Potential findings are actionable in the way that based on the detected findings, the system automatically suggests appropriate scan protocols deviations from the originally planned scan protocol to (better) capture the findings in the actual 3D acquisition to be performed. The medical imaging decision support data may be generated by a rule-based system and/or an AI-based system.

The medical imaging decision support data may comprise, for example, a suggestion to adjust and/or enlarge the 3D scan range or reconstruction field of view to cover the finding in the 3D image. The medical imaging decision support data may comprise, for example, a suggestion to perform additional contrast-enhanced scans e.g. in the case of a dilated aorta detected on topogram images. The medical imaging decision support data may comprise, for example, a suggestion to reconstruct additional 3D images with e.g. dedicated bone kernels to read potential bone fractures or dedicated lung kernels in case of lung nodules detected from topograms.

The medical imaging decision support data may be indicative of a value and/or a value change of a scan parameter of a scan protocol for a 3D medical imaging examination of the patient by a medical imaging device.

In particular, the 3D medical imaging examination of the patient may be performed based on the medical imaging decision support data, thereby obtaining 3D medical imaging data of the patient.

A scan parameter may be, for example, a radiation source parameter of a radiation source, a radiation detector parameter of a radiation detector, a scanning geometry parameter or an injection parameter of a contrast agent injector.

AI-suggested (ad hoc) examination protocol deviations based on topogram findings may reduce the risk of overlooking findings, thereby improving diagnostic quality, and allow for immediate scan protocol adaptations before the actual 3D scan is started, thereby avoiding to call-in the patient another time after the images have been read with associated extra efforts and radiation exposure.

Existing diagnostic applications may be simplified by solving the task on topograms instead of requiring extra CT scans thereby reducing radiation dose.

The medical imaging decision support data may be indicative of a value and/or a value change of a reconstruction parameter of a reconstruction algorithm for reconstructing a medical image based on 3D medical imaging data of the patient. In particular, the 3D medical imaging data of the patient may be provided and/or the medical image may be reconstructed based on the medical imaging decision support data and the 3D medical imaging data of the patient.

One or more example embodiments of the present invention relates in one further aspect to a computer-implemented method for providing a training pair for a training of a machine learning algorithm, the method comprising:

Receiving 3D annotation data in relation to 3D image data of an examination region, the examination region comprising an anatomical structure, the 3D annotation data being indicative of a characteristic of the anatomical structure,
Receiving 2D projection image data, the 2D projection image data being related to the 3D image data through a projection geometry,
Generating 2D annotation data in relation to the 2D projection image data based on the projection geometry and the 3D annotation data, the 2D annotation data being indicative of the characteristic of the anatomical structure, and
Providing the training pair comprising the 2D projection image data and the 2D annotation data.

Thereby consistency between the annotated 2D projection image data and the annotated 3D image data analysis is ensured. Therefore, 2D topogram based artificial intelligence (AI) results can be obtained that are likely more consistent with AI results obtained directly from 3D image data. There may even be a pair of 2D and 3D machine learning algorithms that are basically trained on the same annotations.

In particular, the training pair may comprise the 2D projection image data as an input for the machine learning algorithm and the 2D annotation data as a target output associated with the input.

The characteristic of the anatomical structure may be, for example, a value of a parameter of the anatomical structure, a shape of the anatomical structure, a location of the anatomical structure or combinations thereof.

Topogram-based AI results are likely of higher accuracy compared to algorithms that have been trained only on 2D data where the location and accuracy of ground truth annotations are more limited than in 3D. Additionally, the information which can be extracted by manually annotating the topogram directly, might be significantly inferior to automatically generated annotations from 3D image data. By exploiting information from 3D image data annotations may be created which could not be created by domain experts based on topograms in the first place due to their complexity. In particular, 3D-derived ground truth annotations for 2D AI training may even enable the 2D AI algorithm to capture features that are visibly hidden (impossible to annotate) in 2D topogram data.

Another way to gather accurate labeled training data for 2D topogram AI algorithms from 3D CT images for machine learning tasks in medical imaging is the manual annotation of the relevant anatomical structures by domain experts. Although, this process can be supported by semi-automated tools for the task at hand to minimize user interaction, both the knowledge and time of a domain expert is required. Based on the proposed method, additional training data for machine learning systems which are already trained on a limited set of manually created annotations can be provided, thereby improving their performance.

Furthermore, costs can be lowered due to reduction of manual annotations by domain experts. Machine learning systems can be implemented faster due to faster annotation by algorithms compared to domain experts.

The 3D image data may be received. The 3D annotation data in relation to the 3D image data can be calculated by applying a 3D annotation algorithm onto the 3D image data.

This allows generating annotated training data for 2D topogram-based machine learning systems from 3D image data in a fully automatic manner by exploiting annotation algorithms available for 3D images.

The 2D projection image data can be calculated based on the projection geometry and the 3D image data. Both, the 3D annotation data and the 3D image can be projected into the 2D image space of the medical imaging modality, thereby automatically generating accurate labeled training data for the training of a machine learning algorithm for topogram analysis. The calculated 2D projection image can be referred to as a "synthetic topogram". Physically acquired topograms can be used though.

The 2D projection image data may be a CT topogram of the examination region. In this case, the annotation data need to be projected using the same projection geometry as used to acquire the CT topogram. The 3D image data may be, for example, a whole-body 3D CT image of a human. The 3D image data may be obtained from, for example, trauma scans for which typically whole-body CT reconstructions with a full field of view are performed. The 2D topogram data of the patient may be 2D CT topogram data of the patient.

The examination region may further comprise a surrounding of the anatomical structure. The 3D annotation data may comprise a 3D representation of the anatomical structure. The 2D annotation data may comprise a 2D representation of the anatomical structure. The 3D representation of the anatomical structure and/or the 2D representation of the anatomical structure may delimit the anatomical structure from the surrounding of the anatomical structure.

The 3D annotation data may comprise quantitative information, the quantitative information being indicative of a value of a parameter of the anatomical structure. The 2D annotation data may comprise the quantitative information.

The method can be used for a wide variety of tasks, e.g. detecting lung diseases, fractures and/or coronary calcium. An exemplary application would be the bone density estimation of vertebrae. This is already an existing clinical application which is performed on 3D CT images and thus can be easily leveraged to generate training data for the same application on 2D CT topograms in an automated manner. The anatomical structure may comprise, for example, a vertebrae or a set of vertebrae.

The anatomical structure may comprise a set of vertebrae. The 3D annotation data may comprise, for each vertebrae of the set of vertrebrae, a 3D representation of that vertebrae. The 2D annotation data may comprise, for each vertebrae of the set of vertebrae, a 2D representation of that vertebrae. The 3D annotation data may comprise, for each vertebrae of the set of vertrebrae, a quantitative bone density information, the quantitative bone density information being indicative of a value of a bone density of that vertebrae. The 2D annotation data may comprise, for each vertebrae of the set of vertrebrae, the quantitative bone density information.

One or more example embodiments of the present invention relates in one further aspect to a computer-implemented method for training a machine learning algorithm for topogram analysis, the method comprising:

Receiving a plurality of training pairs, each training pair of the plurality of training pairs being provided based on the described method for providing a training pair for a training of a machine learning algorithm, Training the machine learning algorithm based on the plurality of training pairs.

Each training pair of the plurality of training pairs can be used as an input for the training of the machine learning algorithm. Each training pair of the plurality of training pairs may comprise respective 2D projection image data as an input for the machine learning algorithm and respective 2D annotation data as a target output associated with said input. An accuracy measure of the machine learning algorithm could be determined based on a deviation of a result of the machine learning algorithm, when applied onto a given input, from the target output associated with the given input.

In another aspect, the machine learning algorithm for topogram analysis has been trained according to the described method for training a machine learning algorithm for topogram analysis.

The medical imaging decision support data may be generated based on the outcome of at least two topogram-based AI algorithms, for example, for the detection of metal and/or for the identification of body regions and/or organs.

One or more example embodiments of the present invention relates in one further aspect to a data processing system, comprising a data interface and a processor, the data processing system being configured for carrying out a method according to one of the aspects of one or more example embodiments of the present invention. The data interface may be configured for receiving and/or providing data, in particular, the 3D annotation data, the 2D projection image data, the 3D image data, the 2D topogram data, the training pair and/or the medical imaging decision support data. The processor may be configured for generating and/or calculating data, in particular, the 2D annotation data, the 3D annotation data, the 2D projection image data, the 2D topogram annotation data and/or the medical imaging decision support data.

One or more example embodiments of the present invention relates in one further aspect to a medical imaging device comprising the data processing system. The medical imaging device may be, for example, a computed tomography (CT) device or a magnetic resonance imaging (MRI) device.

The medical imaging device may be a computed tomography device. The 3D image data may be 3D computed tomography image data.

One or more example embodiments of the present invention relates in one further aspect to a computer program product or a computer-readable storage medium, comprising instructions which, when the instructions are executed by a computer, cause the computer to carry out the method according to one of the aspects of one or more example embodiments of the present invention.

Any of the algorithms mentioned herein, in particular the machine learning algorithm and/or the 3D annotation algorithm, can be based on one or more of the following architectures: convolutional neural network, deep belief network, random forest, deep residual learning, deep reinforcement learning, recurrent neural network, Siamese network, generative adversarial network or auto-encoder. In particular, the trained machine learning algorithm can be embodied as a deep learning algorithm, in particular as a deep convolutional neural network. Throughout the present disclosure, the term "artificial intelligence (AI) algorithm" is used synonymously for the term "machine learning algorithm".

The computer program product can be, for example, a computer program or comprise another element apart from the computer program. This other element can be hardware, for example a memory device, on which the computer program is stored, a hardware key for using the computer program and the like, and/or software, for example, a documentation or a software key for using the computer program. A computer-readable storage medium can be embodied as non-permanent main memory (e.g. random-access memory) or as permanent mass storage (e.g. hard disk, USB stick, SD card, solid state disk).

The data processing system can comprise, for example, at least one of a cloud-computing system, a distributed computing system, a computer network, a computer, a tablet computer, a smartphone or the like. The data processing system can comprise hardware and/or software. The hardware can be, for example, a processor system, a memory system and combinations thereof. The hardware can be configurable by the software and/or be operable by the software. Calculations for performing an action of a method may be carried out in the processor.

Data, in particular each of the 3D annotation data, the 2D projection image data, the 3D image data and the 2D topogram data, can be received, for example, by receiving a signal that carries the data and/or by reading the data from a computer memory. Data, in particular each of the training pair and the medical imaging decision support data, can be provided, for example, by transmitting a signal that carries the data and/or by writing the data into a computer memory and/or by displaying the data on a display.

In the context of the present invention, the expression "based on" can in particular be understood as meaning "using, inter alia". In particular, wording according to which a first feature is calculated (or generated, determined etc.) based on a second feature does not preclude the possibility of the first feature being calculated (or generated, determined etc.) based on a third feature.

Reference is made to the fact that the described methods and the described systems are merely preferred example embodiments of the invention, and that the invention can be varied by a person skilled in the art, without departing from the scope of the invention as it is specified by the claims.

FIG. 1 shows an annotated 3D image M3 in form of a rendered thorax 3D CT image comprising 3D representations of the vertebrae V1, V2 of the set V of vertebrae and further comprising 3D representations of ribs R1, R2 of the rib cage R.

Figure 2:
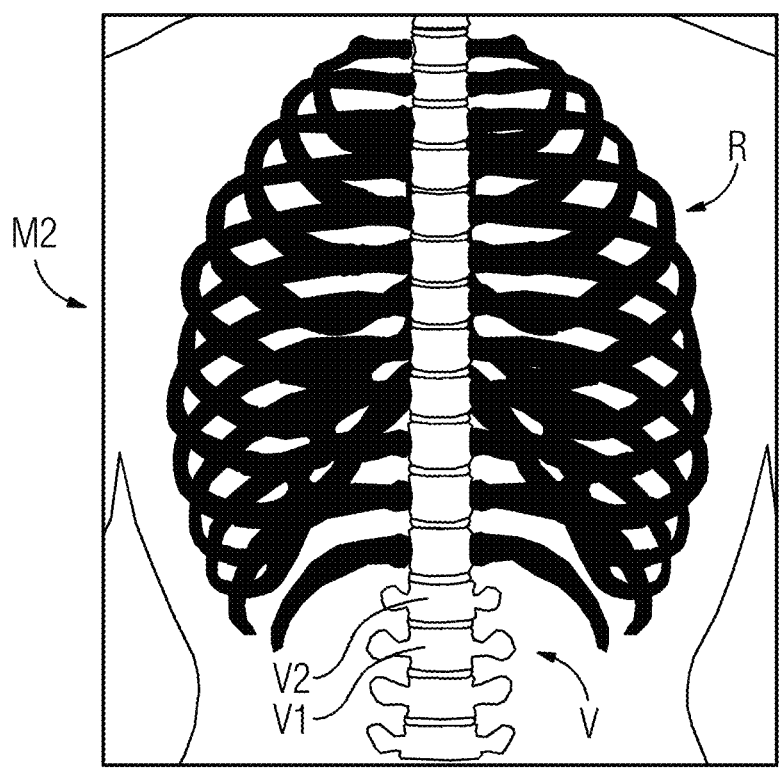
FIG. 2 shows an annotated 2D projection image according to an example embodiment.

FIG. 2 shows an annotated 2D projection image M2 in form of a synthetic topogram with 2D representations of the vertebrae V1, V2. The synthetic topogram has been calculated from the thorax 3D CT image based on a coronal projection geometry. The vertebrae V1, V2 are automatically segmented from the 3D CT image and then projected into the thereof synthetically created topogram image. A set of similarly generated topograms now can be used to train a machine learning system to detect vertebrae in actual topograms.

FIG. 3 shows a flow chart for a computer-implemented method for providing a training pair for a training of a machine learning algorithm, the method comprising:
  Receiving T1 3D annotation data in relation to 3D image data of an examination region, the examination region comprising an anatomical structure, the 3D annotation data being indicative of a characteristic of the anatomical structure,
  Receiving T2 2D projection image data, the 2D projection image data being related to the 3D image data through a projection geometry,
  Generating T3 2D annotation data in relation to the 2D projection image data based on the projection geometry and the 3D annotation data, the 2D annotation data being indicative of the characteristic of the anatomical structure, and
  Providing 14 the training pair comprising the 2D projection image data and the 2D annotation data.

FIG. 4 shows a flow chart for another example of a method for providing a training pair, the method further comprising:
  Receiving T10 the 3D image data,
  Calculating T11 the 3D annotation data in relation to the 3D image data by applying a 3D annotation algorithm onto the 3D image data, and
  Calculating T12 the 2D projection image data based on the projection geometry and the 3D image data.

FIG. 5 shows a flow chart for a computer-implemented method for training a machine learning algorithm for topogram analysis, the method comprising:
  Receiving S11 a plurality of training pairs, each training pair of the plurality of training pairs being provided based on the method for providing a training pair,
  Training S12 the machine learning algorithm based on the plurality of training pairs.

Figure 6:
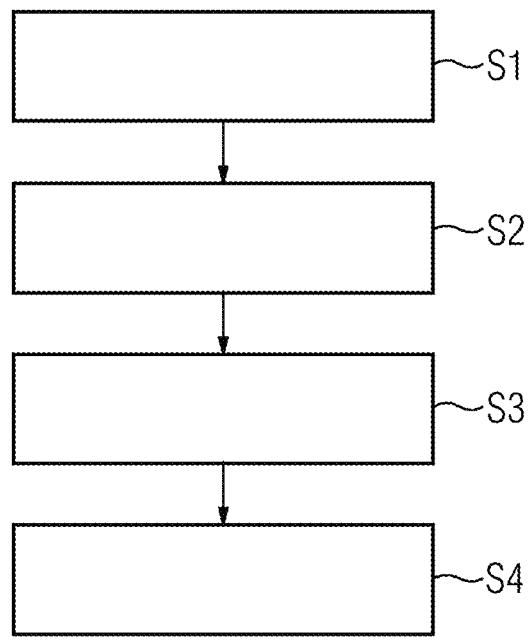
FIG. 6 shows a flow chart for a method for providing medical imaging decision support data according to an example embodiment.

FIG. 6 shows a flow chart for a computer-implemented method for providing medical imaging decision support data, the method comprising:
  Receiving S1 2D topogram data of a patient,
  Generating S2 2D topogram annotation data by applying a machine learning algorithm for topogram analysis onto the 2D topogram data,
  Generating S3 the medical imaging decision support data based on the 2D topogram annotation data, and
  Providing S4 the medical imaging decision support data.

Figure 7:
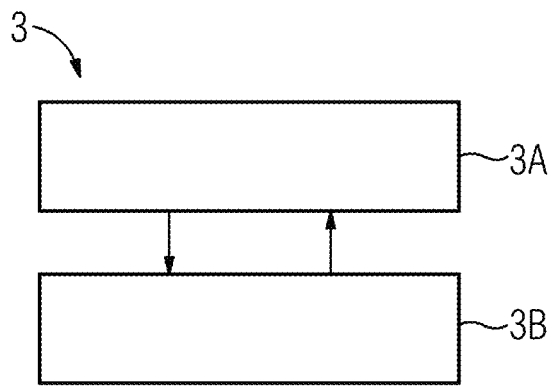
FIG. 7 shows a data processing system according to an example embodiment.

FIG. 7 shows a data processing system 3 comprising a data interface 3A and a processor 3B, the data processing system 3 being configured for carrying out a method as described with respect to one of the FIGS. 3-6.

Although some example embodiments of the present invention have been disclosed in the form of preferred embodiments and variations thereon, it will be understood that numerous additional modifications and variations could be made thereto without departing from the scope of example embodiments of the present invention. For the sake of clarity, it is to be understood that the use of "a" or "an" throughout this application does not exclude a plurality, and "comprising" does not exclude other steps or elements. The mention of a "unit", "module" or a "device" does not preclude the use of more than one unit or device.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'unit', interface' or the term 'controller' may be replaced with the term 'circuit.' The term 'module' and may 'unit' refer to, be part of, or include processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention is not limited to the example embodiments described hereinto fore. Rather, other variants of the invention can also be derived herefrom by the person skilled in the art, without departing from the subject matter of the invention. In particular, it is furthermore possible to combine all the individual features described in connection with the example embodiment with one another in a different way also, without departing from the subject matter of the invention.

The invention claimed is:

1. A computer-implemented method for providing a training pair for a training of a machine learning algorithm, the method comprising:
    receiving 3D annotation data in relation to 3D image data of an examination region, the examination region comprising an anatomical structure, the 3D annotation data being indicative of a characteristic of the anatomical structure;
    receiving 2D projection image data, the 2D projection image data being related to the 3D image data through a projection geometry;
    generating 2D annotation data in relation to the 2D projection image data based on the projection geometry and the 3D annotation data, the 2D annotation data being indicative of the characteristic of the anatomical structure; and
    providing the training pair, the training pair comprising the 2D projection image data and the 2D annotation data,
    wherein the 2D projection image data is a CT topogram of the examination region.

2. The method of claim 1, further comprising:
    receiving the 3D image data; and
    calculating the 3D annotation data in relation to the 3D image data by applying a 3D annotation algorithm onto the 3D image data.

3. The method of claim 2, wherein
    the 3D annotation data includes a 3D representation of the anatomical structure, and
    the 2D annotation data includes a 2D representation of the anatomical structure.

4. The method of claim 1, further comprising:
    receiving the 3D image data; and
    calculating the 2D projection image data based on the projection geometry and the 3D image data.

5. The method of claim 4, wherein
    the 3D annotation data includes a 3D representation of the anatomical structure, and
    the 2D annotation data includes a 2D representation of the anatomical structure.

6. The method of claim 1, wherein
    the 3D annotation data includes a 3D representation of the anatomical structure, and
    the 2D annotation data includes a 2D representation of the anatomical structure.

7. The method of claim 1, wherein
    the anatomical structure includes a set of vertebrae,
    the 3D annotation data including, for each vertebrae of the set of vertebrae, a 3D representation of that vertebrae, and
    the 2D annotation data comprising, for each vertebrae of the set of vertebrae, a 2D representation of that vertebrae.

8. The method of claim 7, wherein
    the 3D annotation data includes, for each vertebrae of the set of vertebrae, a quantitative bone density information, the quantitative bone density information being indicative of a value of a bone density of that vertebrae, and
    the 2D annotation data includes, for each vertebrae of the set of vertebrae, the quantitative bone density information.

9. A computer-implemented method for training a machine learning algorithm for topogram analysis, the method comprising:
    receiving a plurality of training pairs, each training pair of the plurality of training pairs being provided using the method of claim 1; and
    training the machine learning algorithm based on the plurality of training pairs.

10. The method of claim 1, wherein the 2D annotation data is automatically generated from the 3D image data.

11. The method of claim 10, wherein the 2D annotation data is automatically generated based on one or more annotation algorithms available for 3D images.

* * * * *